United States Patent [19]

Endo et al.

[11] Patent Number: 5,264,572
[45] Date of Patent: Nov. 23, 1993

[54] CATALYST FOR ISOCYANATE TRIMERIZATION

[75] Inventors: Takeshi Endo, Kanagawa; Yoko Nambu, Tokyo, both of Japan

[73] Assignee: Asahi Denka Kogyo K.K., Tokyo, Japan

[21] Appl. No.: 939,405

[22] Filed: Sep. 1, 1992

Related U.S. Application Data

[62] Division of Ser. No. 661,546, Feb. 26, 1991, abandoned.

[30] Foreign Application Priority Data

Mar. 12, 1990 [JP] Japan .................................. 2-62427

[51] Int. Cl.$^5$ ............................................ C07D 251/34
[52] U.S. Cl. ...................................................... 544/193
[58] Field of Search ........................................... 544/193

[56] References Cited

U.S. PATENT DOCUMENTS

| | | | |
|---|---|---|---|
| 3,898,293 | 8/1975 | Deem | 502/164 |
| 4,621,149 | 11/1986 | Fukuoka et al. | 544/172 |
| 4,960,848 | 10/1990 | Scholl et al. | 528/48 |
| 4,992,548 | 2/1991 | Scholl | 544/143 |

FOREIGN PATENT DOCUMENTS

| | | |
|---|---|---|
| 0315692 | 5/1989 | European Pat. Off. . |
| 0339396 | 11/1989 | European Pat. Off. . |
| 1130448 | 5/1962 | Fed. Rep. of Germany . |
| 2256153 | 7/1975 | France . |
| 63-287773 | 11/1988 | Japan . |
| 63-290871 | 11/1988 | Japan . |
| 845827 | 8/1960 | United Kingdom . |
| 1464788 | 2/1977 | United Kingdom . |

OTHER PUBLICATIONS

Chemical Abstracts, vol. 106, No. 9, Feb. 2, 1987, Abstract No. 67264q, W. Broda et al., "Applications of Phase-Transfer Catalysis", etc.

Synthesis, Alkali Metal Fluorides in Organic Synthesis, No. 3, 1983, pp. 169–184.

*Primary Examiner*—John M. Ford
*Attorney, Agent, or Firm*—Flynn, Thiel, Boutell & Tanis

[57] ABSTRACT

A process for producing an isocyanate trimer and a process for producing an urethane with a catalyst for isocyanate trimerization or urethane formation, which comprises cesium fluoride or a tetraalkylammonium fluoride.

1 Claim, No Drawings

CATALYST FOR ISOCYANATE TRIMERIZATION

This application is a division of U.S. patent application Ser. No. 07/661,546, filed Feb. 26, 1991 now abandoned.

BACKGROUND OF THE INVENTION

The invention relates to a catalyst for isocyanate trimerization and urethane formation or urethanization. It further relates to a process for producing an isocyanate trimer and a process for producing an urethane.

PRIOR ART

Since an isocyanurate structure obtained by trimerizing an organic isocyanate brings about an improvement in properties such as enhanced thermal resistance, flame retardancy, chemical resistance, etc., for polyurethane, coating material and the like, investigation has heretofore been made on a number of catalysts for isocyanate trimerization. For example, various metal salts of carboxylic acids, metal salts of DMF, tertiary amines, alcoholates of metals, etc., are effective catalysts for the above purpose. In addition, an epoxide/pyridine selectively forms a trimer. [see J. I. Jones et al., J. Chem. Soc., 4392(1957)].

However, conventional catalysts for isocyanate trimerization, as mentioned above, have suffered the following disadvantages:

① insufficient activity, which necessitates severe reaction conditions,

② insufficient selectivity accompanied by the formation of by-products such as dimers, carbodiimides, etc., ③ difficulty in eliminating high-boiling additives such as DMF, and ④ inevitable side reactions due to the attack by the active species of a catalyst upon functional groups such as ester, silyl ether, etc., in the system containing such groups.

Shiomura et al. have recently reported in Japanese Patent Laid-Open Nos. 287773/1988 and 290871/1988, etc., the trimerization of organic isocyanates in the presence of potassium fluoride alone or together with polyethylene oxide as a phase-transfer catalyst. However, sufficient activity cannot be obtained in the presence of a single catalyst.

It has been a usual practice in the production of a polyurethane having an isocyanurate structure to use a complex system containing a trimerization catalyst and a urethanization catalyst, for example, a catalyst mixture of potassium acetate and a tertiary amine.

On the other hand, the present inventors have already discovered a selective ring-opening reaction of a glycidyl ether with an aryl silyl ether using cesium fluoride as the catalyst (see Japanese Patent Laid-Open No. 57981/1988; Y. Nambu, T. Endo, Tetrahedron Lett.,31, 1723(1990) in Press) and are advancing investigations on a variety of organic reactions by the use of fluoride catalysts.

An object of the present invention is to provide a catalyst for isocyanate trimerization and a catalyst for urethanization, each being improved over the above-mentioned disadvantages, and processes for producing an isocyanate trimer and urethane, respectively by the use of the catalyst.

SUMMARY OF THE INVENTION

The catalyst for isocyanate trimerization or urethane formation or urethanization of the invention comprises cesium fluoride or a tetraalkylammonium fluoride.

In the process for producing an isocyanate trimer according to the present invention, cesium fluoride or a tetraalkylammonium fluoride is used as the catalyst.

Further, in the process for producing a urethane according to the present invention, cesium fluoride or a tetraalkylammonium fluoride is used as the catalyst.

The cesium fluoride catalyst according to the present invention is used in a sufficiently dried state. The alkyl groups of the tetraalkylammonium fluoride are exemplified by the alkyl groups each having 1 to 10 carbon atoms, and are preferably methyl, ethyl and butyl. The above ammonium salts are available in the form of hydrates and ready for use as such. However, the reaction product can be improved in purity when the salt is dried prior to its use. Tetrabutylammonium fluoride having a lower moisture content is available from, e.g., Tokyo Kasei K.K., in the form of its tetrahydrofuran solution (1 mol/l).

The amount of the catalyst to be used in the present invention ranges desirably from 0.001 to 0.1 equivalent, more desirably from 0.005 to 0.05 equivalent on the basis of the isocyanate.

The isocyanate to be used in the trimerization or urethanization according to the present invention is exemplified by those having a substituted or unsubstituted alkyl or aryl group. The reaction proceeds selectively even when the isocyanate has a halide, ester, isocyanate, alkyl ester, aryl ester, silyl ether, ether, amide, ketone, unsaturated carbon, nitro, or the like group as the substituent.

The compound having a hydroxyl group which is used in the urethanization reaction according to the present invention is exemplified by substituted or unsubstituted, monofunctional or multifunctional, straight-chain or branched alcohol and substituted or unsubstituted aromatic compound having a hydroxyl group.

The process for producing the isocyanate trimer or urethane can be put to practice without any solvent or in an aprotic polar solvent. Examples of the aprotic polar solvent include acetonitrile, acetone, DMF, and THF. The proper amount of the solvent to be used ranges from 0.3 to 2 equivalents on the basis of the isocyanate.

In what follows, the preferred embodiments of the present invention will be described.

The trimerization is carried out by reacting an organic isocyanate at a temperature of from room temperature to 150° C. for one minute to 2 hours without any solvent by using either 0.005 to 0.02 equivalent of cesium fluoride or a tetraalkylammonium fluoride as the catalyst. After the reaction, an unreacted isocyanate is removed under a reduced pressure, the reaction product is dissolved in methylene chloride, the catalyst is separated by filtration and the methylene chloride solvent is distilled away to obtain an isocyanurate corresponding to the starting isocyanate.

The urethanization and trimerization accompanied by urethanization are carried out by reacting an organic isocyanate with 0.1 to 1 equivalent of an organic hydroxylic compound under the almost same conditions as those described above to obtain a urethane and an isocyanurate corresponding to the starting isocyanate.

EFFECT OF THE INVENTION

The cesium fluoride and tetraalkylammonium fluoride catalysts according to the present invention are novel and highly active catalysts useful for isocyanate trimerization and urethanization.

The use of these catalysts according to the present invention enables the trimerization of organic isocyanates to proceed under milder conditions than the use of conventional catalysts and thereby obtain isocyanurate derivatives having a high purity. Furthermore, the catalysts according to the present invention exhibit such a high selectivity for the trimerization of isocyanates that they can be applied to the synthesis of novel isocyanurate derivatives having a variety of reactive groups.

Moreover, the catalysts according to the present invention are effective for the reaction of an organic isocyanate with a compound having a hydroxyl group to produce a urethane and an isocyanate quantitatively in a ratio corresponding to the feed ratio of the above two raw materials under mild reaction conditions. Thus, the catalysts according to the present invention are highly effective for the production of a polyurethane having excellent performances and, furthermore, exhibit high activity in the reaction of isocyanates with phenols of low reactivity and are capable of being utilized in synthesizing masked isocyanates.

EXAMPLES

The present invention will now be described in more detail by the following Examples, but shall not be limited thereto.

EXAMPLE 1

1.28 g (8.4 mmol) of cesium fluoride was weighed into a flask and dried under a reduced pressure at 130° C. for 30 minutes. When 50 g (0.42 mol) of phenyl isocyanate was added thereto with stirring and heating at 130° C., the mixture in the system solidified after one minute. After 4 minutes of further heating, an unreacted phenyl isocyanate was removed under a reduced pressure, the residue was dissolved in methylene chloride, the catalyst was separated by filtration and thereafter the solvent was distilled away to obtain 45 g of triphenyl isocyanurate at a yield of 90.5%. The structure of the product was confirmed by the melting point (285° C.), NMR and IR. No formation of a dimer was observed.

EXAMPLE 2

The same reaction system as that in Example 1 was allowed to react at room temperature for 20 minutes, followed by the same treatment as that in Example 1 to obtain 45 g of a solid. By washing the solid with ether, 40.1 g of triphenyl isocyanurate was obtained at a yield of 80.2% as ether-insoluble along with 4.4 g of a dimer at a yield of 8.8% as ether-soluble.

EXAMPLE 3

To 50 g (0.42 mol) of phenyl isocyanate was added 8.3 ml (8.4 mmol) of a solution of tetrabutylammonium fluoride in THF (1 mol/l) with sufficient stirring at room temperature. After 40 seconds, the mixture in the system solidified. After one minute, an unreacted phenyl isocyanate was distilled away under a reduced pressure and the residue was treated in the same manner as that in Example 2 to obtain 42.6 g of triphenyl isocyanurate at a yield of 85.1% as ether-insoluble along with 6.35 g of a dimer at a yield of 12.7% as ether-soluble.

EXAMPLE 4

The procedure of Example 3 was repeated with tetrabutylammonium fluoride trihydrate, instead of the solution of tetrabutylammonium fluoride in THF, being stirred for 1.5 minutes at room temperature. Thus, 40.7 g of triphenyl isocyanurate was obtained at a yield of 81.3% along with 8.75 g of a dimer at a yield of 17.5%.

COMPARATIVE EXAMPLES 1 TO 3

The procedure of Example 2 was repeated with various catalysts (2 mol %) listed in Table 1 instead of cesium fluoride to conduct reaction.

Tables 1 and 1A shows the results of Comparative Examples 1 to 3 as well as those of Examples 1 to 4. As obvious from Table 1, the use of cesium fluoride or tetrabutylammonium fluoride as the catalyst enabled the trimer to be produced at a high yield in a short time.

TABLE 1

|  | Catalyst | Reaction temp. | Reaction time (min) | Yield (%) Trimer | Dimer |
|---|---|---|---|---|---|
| Example 1 | CsF | 130° C. | 5 | 90.5 | 0 |
| Example 2 | CsF | room temp. | 20 | 80.2 | 8.8 |
| Example 3 | Bu$_4$NF/THF | room temp. | 1 | 85.1 | 12.7 |
| Example 4 | Bu$_4$NF/3H$_2$O | room temp. | 1.5 | 81.3 | 17.5 |

TABLE 1A

|  | Catalyst | Reaction temp. | Reaction time (min) | Yield (%) Trimer | Dimer |
|---|---|---|---|---|---|
| Comp. Ex. 1 | AcOK | " | 20 | 0 | 0 |
| Comp. Ex. 2 | Et$_3$N | " | 20 | 0 | 0 |
| Comp. Ex. 3 | KF | " | 20 | 1.4 |  |

Remarks

Bu, Ac and Et indicate butyl, acetyl and ethyl, respectively.

EXAMPLE 5

In the same manner as that in Example 1, 4-allyloxyphenyl isocyanate was heated at 130° C. for 10 minutes with stirring in the presence of cesium fluoride as the catalyst (2 mol %), and the resultant solidified product was recrystallized from ethanol to obtain tris(4-allyloxyphenyl) isocyanurate at a yield of 85.4%.

Melting point: 218°–220° C.
Elemental analysis:

| | Elemental analysis: | | |
|---|---|---|---|
|  | C | H | N |
| Found (%) | 68.79 | 5.31 | 8.06 |
| Calculated (%) | 68.56 | 5.13 | 8.00 |

EXAMPLE 6

In the same manner as that in Example 1, 4-nitrophenyl isocyanate was heated at 150° C. for 1 hour with stirring in the presence of cesium fluoride as the catalyst (2 mol %), and tris(4-nitrophenyl) isocyanurate was obtained at a yield of 75%.

Melting point: 275°–277 °C.

| Elemental analysis result: | | | |
| --- | --- | --- | --- |
| | C | H | N |
| Found (%) | 51.35 | 2.63 | 17.35 |
| Calculated (%) | 51.22 | 2.46 | 17.07 |

EXAMPLES 7 TO 9

In the same manner as that in Example 1. Using cesium fluoride or in Example 3 using tetrabutylammonium fluoride, n-butyl isocyanate was reacted under the reaction conditions specified in Table 2 in the presence of cesium fluoride alone, a cesium fluoride/trimethylsilyl phenoxide system or tetrabutylammonium fluoride (1M THF solution) as the catalyst (2 mol %), and tributyl isocyanurate was obtained at the yields given in Table 2, even for the above alkyl isocyanate having low reactivity:

$^1$H-NMR(CDCl$_3$) δ: 0.8–2.0 ppm [m, 21H, CH$_3$(CH$_2$)$_2$], 3.88[t, 6H, CH$_2$N]

TABLE 2

| | Catalyst | Reaction temp. | Reaction time | Yield (%) |
| --- | --- | --- | --- | --- |
| Example 7 | CsF | 130° C. | 60 min | 62.0 |
| Example 8 | CsF/PhOSiMe$_3$ | 130° C. | 10 min | 95.0 |
| Example 9 | Bu$_4$NF/THF | 70° C. | 60 min | 83.5 |

As shown in Table 2, the combined use of cesium fluoride an alkyl or aryl silyl ether can enhance the yield of the objective product.

EXAMPLE 10

1.28 g (8.4 mmol) of cesium fluoride was weighed into a flask and dried under a reduced pressure at 130° C. for 30 minutes. When 50 g (0.42 mol) of phenyl isocyanate and 6.43 ml (0.084 mol) of isopropanol were added thereto at room temperature with stirring, a large amount of heat was evolved in the mixture resulting in solidification in 20 seconds. After 2 minutes, an unreacted raw material was removed from the system under a reduced pressure to obtain 52.0 g of a solid at a yield of 94.5%. From the ether-soluble solid, 13.1 g of isopropyl N-phenylcarbamate was obtained as the urethanization produce at a yield of 88.0% based on the starting isopropanol. The chemical structure of the product had a melting point of 83° to 84° C. as was confirmed by $^1$H-NMR and IR. In addition, 38.9 g of triphenyl isocyanurate was obtained as the trimerization product as ether-insoluble.

EXAMPLE 11

To a liquid mixture of 50 g (0.42 mol) of phenyl isocyanate and 5.82 ml (0.076 mol) of isopropanol was added 8.3 ml (8.4 mmol) of a solution of tetrabutylammonium fluoride in THF (1 mol/l) with sufficient stirring at room temperature. After 1 minute, the mixture in the system solidified. After 5 minutes in total, an unreacted raw material was distilled away under a reduced pressure to obtain reaction products almost quantitatively including 16.7% of isopropyl N-phenylcarbamate and 82.0% of triphenyl isocyanurate.

COMPARATIVE EXAMPLE 4

A liquid mixture of 50 g (0.42 mol) of phenyl isocyanate and 6.43 ml (0.084 mol) of isopropanol was stirred at room temperature for 20 minutes and thereafter an unreacted raw material was distilled away under a reduced pressure to obtain 16.1% of isopropyl N-phenylcarbamate.

EXAMPLE 12

1.28 g (8.4 mmol) of cesium fluoride was weighed into a flask and dried under a reduced pressure at 130° C. for 30 minutes. 50 g (0.42 mol) of phenyl isocyanate and 39.5 g (0.42 mol) of phenol were added thereto with stirring at 105° C. for 10 minutes, followed by the removal of an unreacted raw material at a reduced pressure. Thus, 88.3 g of phenyl N-phenylcarbamate having a melting point of 123° to 124° C. was obtained at a yield of 93.1%.

COMPARATIVE EXAMPLE 5

The procedure of Example 12 was repeated except that no catalyst was added to the reaction system. As a result, 8.3 g of phenyl N-phenylcarbamate was obtained at a yield of 9.3%.

We claim:

1. In a process for producing an isocyanate trimer, the improvement characterized by using cesium fluoride as a catalyst.

* * * * *